United States Patent
Lüdeke et al.

(10) Patent No.: US 6,236,205 B1
(45) Date of Patent: May 22, 2001

(54) MR DEVICE PROVIDED WITH A MEDICAL INSTRUMENT, AND METHOD OF DETERMINING THE POSITION OF THE MEDICAL INSTRUMENT

(75) Inventors: Kai-Michael Lüdeke; Volker Rasche, both of Hamburg (DE)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/212,624

(22) Filed: Dec. 16, 1998

(30) Foreign Application Priority Data

Dec. 16, 1997 (DE) ................................. 197 55 782

(51) Int. Cl.[7] ........................................ G01V 3/00
(52) U.S. Cl. ........................ 324/318; 324/322; 324/300
(58) Field of Search .................................. 324/307, 318, 324/300; 600/410, 322

(56) References Cited

U.S. PATENT DOCUMENTS 5,274,330 * 12/1993 Rindlisbacher et al. ............. 324/307
5,353,795 * 10/1994 Souza et al. ....................... 128/653.2

* cited by examiner

*Primary Examiner*—Jay Patidar
*Assistant Examiner*—Brij B. Shrivastav
(74) *Attorney, Agent, or Firm*—John F. Vodopia

(57) ABSTRACT

The invention relates to a magnetic resonance (MR) device which is provided with a medical instrument (10) which is to be introduced into an object (1) to be examined, and also with a coil system (11) which is arranged in or on the instrument (10) and includes at least one coil for receiving and/or transmitting an RF signal, to a medical instrument (10) of this kind and also to a method of determining the position of such a medical instrument (10) that can be introduced into an object (1) to be examined. According to the invention the coil system (11) in an MR device of this kind forms a resonant circuit (20) in conjunction with a capacitor (19) and a modulation unit (12) is provided in order to modulate an RF signal coupled into the coil system (11).

18 Claims, 3 Drawing Sheets

MR DEVICE PROVIDED WITH A MEDICAL INSTRUMENT, AND METHOD OF DETERMINING THE POSITION OF THE MEDICAL INSTRUMENT

BACKGROUND OF THE INVENTION

1. Field of the Invention

The invention relates to a magnetic resonance (MR) device which is provided with a medical instrument which is to be introduced into an object to be examined, and also with a coil system which is arranged in or on the instrument and includes at least one coil for receiving and/or transmitting an RF signal. The invention also relates to a medical instrument to be introduced into an object to be examined, notably a catheter or an endoscope, provided with a coil system which is arranged in or on the instrument and includes at least one coil for receiving and/or transmitting an RF signal, as well as to a method of determining the position of a medical instrument that can be introduced into an object to be examined.

2. Description of Related Art

Such an MR device, medical instrument and method of determining the position thereof are known from U.S. Pat. No. 5,353, 795. Therein, a small RF coil, being a so-called microcoil, is arranged in a catheter which is introduced into a patient. During operation of the MR device, an RF signal is induced into the microcoil after excitation of the examination zone, which RF signal is applied, via an RF lead, to a receiver device which processes the signal and determines the position of the coil. The position can be superposed on an image, for example an MR image or a computer tomography (CT) image.

It has been found that the RF lead required between the transmitter and/or receiver device, arranged outside the object to be examined, to a microcoil which is preferably attached to the tip of the medical instrument constitutes a drawback. There is a risk of heating of tissue due to resonance (notably X/4 resonance) occurring in the vicinity of the RF lead during the transmission phase (RF excitation) of the MR examination. Furthermore, the RF lead must inherently be formed by very thin wires, because the medical instrument must also be introduced into very thin veins for various applications. Consequently, substantial signal losses may occur during the transmission of the signal received by the microcoil to a receiving device. Moreover, in conjunction with the RF lead the microcoil must form a stable resonant circuit; therefore, the length of the RF lead cannot be changed at random. Moreover, the known device requires a separate receiving channel for the microcoil or (when a single receiving channel is used) a switching device is required for switching over between the receiving coil system and the microcoil.

SUMMARY OF THE INVENTION

It is an object of the present invention to provide an improved MR device, an improved medical instrument and an improved method of determining the position of such a medical instrument while avoiding notably said drawbacks.

In respect of the MR device and in respect of the medical instrument this object is achieved according to the invention in that the coil system constitutes a resonant circuit in conjunction with a capacitor, and that there is provided a modulation unit for modulating an RF signal coupled into the coil system.

The RF lead to a transmitter device which is arranged outside the object to be examined as well as the transmitter device itself can be dispensed with in the MR device according to the invention, because the signal induced into the coil system is modulated, after RF excitation of the part of the object to be examined which is present in an examination zone, and emitted again with this modulated frequency and/or phase. Using a receiving coil system which forms part of the MR device, the (modulated) coil signal transmitted by the coil system as well as an object signal from the excited zone of the object to be examined are received as an MR signal. Because these signals have different frequencies and/or phases, the coil signal and the object signal can be simply separated, so that the determination of the position of the coil system, and hence of the position of the medical instrument, is also simply possible.

The drawbacks described for an RF lead no longer occur in the MR device according to the invention, because low-loss transmission of RF signals is necessary neither from the coil system to the receiving system nor in the opposite direction. The low-ohmic RF leads required in the known MR device, therefore, may be replaced by extremely thin, high-ohmic leads. Thus, the risk of heating of tissue is also eliminated in the MR device according to the invention and no additional receiving channel or switching device is required either.

The elements of the resonant circuit and the modulation unit in the preferred embodiment defined in claim 2 neighbor one another; for example, they are situated at a distance of a few millimeters to centimetres from one another, offering the advantage that no or only very short RF leads are required between these elements.

The control lead in the further embodiment of the invention as defined in claim 3 preferably consists of a high-ohmic two-wire lead whose length may be chosen at random and via which a low-frequency control signal is applied to the modulation unit by the control unit. The control unit is preferably arranged outside the object to be examined.

A particularly simple implementation of the control lead is that disclosed in claim 4 in which the control signal is supplied in an optical manner and is converted into an electrical control signal by means of suitable means, for example a type of optocoupler.

The modulation unit may have a very simple and compact construction and comprises essentially a switch arrangement as disclosed in claim 5 which can be manufactured so as to be very compact. The switch arrangement is preferably switched between two states for the modulation of the oscillation of the resonant circuit.

The preferred embodiment disclosed in claim 6 constitutes a fully wireless solution in which the control signal is induced into an RF receiving system as an RF control signal and the actual control signal for the resonant circuit is converted. The frequency of the RF control signal is then substantially higher or lower than the frequency of the signal induced into the coil system and also substantially higher or lower than the resonant frequency of the resonant circuit so as to avoid disturbances. Preferably, the RF receiving system is also arranged very close to the modulation unit and the resonant circuit, for example at a distance of a few centimeters.

The embodiment defined in claim 8 enables notably determination of the position of the medical instrument in a rather large zone, in which the coils are arranged, by determining the position of the individual coils whose position in or on the instrument is known.

In accordance with claim 9, it is also possible to provide a plurality of resonant circuits which are also modulated in a different manner, for example with different frequencies, so that the position of each individual coil system can be unambiguously determined, for example by reproducing each coil system in a different image zone.

The object in respect of the method of determining the position of a medical instrument is achieved in that the coil system constitutes a resonant circuit in conjunction with a capacitor, that an RF signal which is coupled into the coil system is modulated in such a manner that the MR signal contains a modulated coil signal, and that the position of the instrument is determined from the coil signal.

The method according to the invention enables significantly simpler determination of the position of the coil system in comparison with the known method. As a result of the modulation according to the invention, in which a frequency shift or a phase shift is imposed on the signal induced into the coil system, the modulated coil signal emitted again by the coil system can be separated from the MR signal received by the receiving coil system by means of a simple calculation method.

The claims 12 to 14 disclose attractive versions of the method according to the invention, especially attractive versions of the modulation.

BRIEF DESCRIPTION OF THE DRAWINGS

The invention will be described in detail hereinafter with reference to the drawing. Therein.

DETAILED DESCRIPTION OF THE PREFERRED EMBODIMENT

Figure 1:
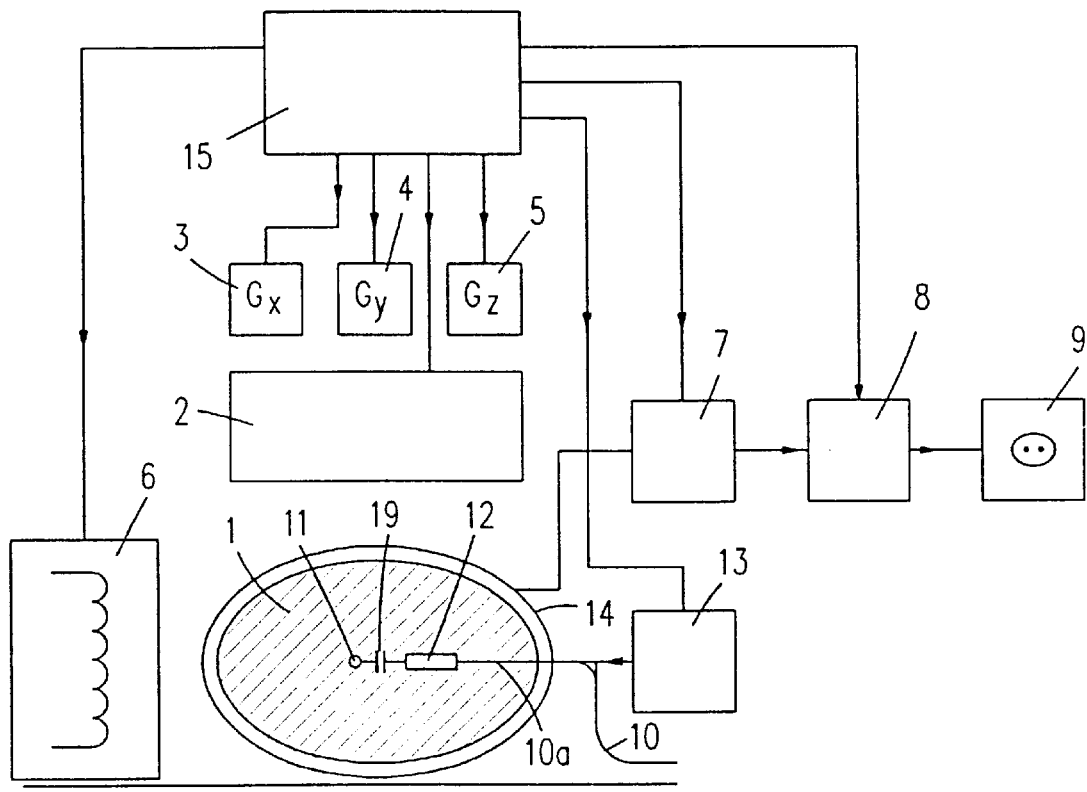
FIG. 1 shows a block diagram of an MR device according to the invention.

The reference 1 in FIG. 1 denotes an object to be examined which is situated in an examination zone exposed to a uniform, steady magnetic field which is generated by a main field magnet 2. The steady, uniform magnetic field can be modified by means of three gradient systems 3, 4, 5 which generate a magnetic gradient field which extends in the direction of the uniform, steady magnetic field and has a gradient in the x direction, the y direction or the z direction. Also provided is an RF transmitter 6 which is capable of pulse-wise generating an RF magnetic field in the examination zone.

The object signals generated in the object to be examined are detected by a receiving coil system 14, which may consist of one or more receiving coils, in conjunction with a receiving device 7. On the basis of the digitized object signals and after a suitable transformation, for example a Fourier transformation, the nuclear magnetization distribution in the examination zone is reconstructed in a reconstruction unit 8 and displayed in the form of an MR image on a display unit 9.

A medical instrument 10, for example a catheter, is introduced into the object 1 to be examined; at the tip of this instrument there is provided a microcoil 11 which may have a construction as described in US 5,353,795. In or on the part 10a of the catheter 10 introduced into the object 1 to be examined, a capacitor 19 which constitutes a resonant circuit in conjunction with the microcoil 11 and a modulation unit 12 are arranged in the vicinity of the microcoil 11. The modulation unit 12 is controlled by a control unit 13. The modulated coil signal, induced into the microcoil 11 and emitted again by the microcoil 11 after modulation by the modulation unit 12, is also picked up by the receiving coil system 14 (the coil signal of the microcoil is coupled into the receiving coil system 14) and processed by the components 7, 8. The components 2 to 8 as well as 13 are controlled by a programmable control unit 15.

Figure 2:
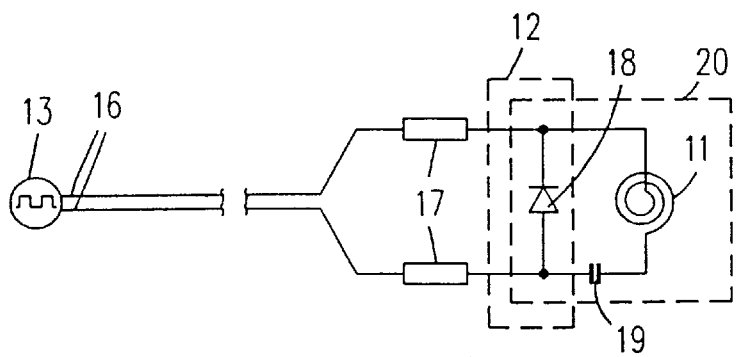
FIG. 2 shows an equivalent diagram of a first embodiment of the invention.

FIG. 2 shows a first embodiment of the invention. The microcoil 11 forms, in conjunction with the capacitor 19, a resonant circuit 20 whose resonance frequency is tuned to the Larmor frequency of the tissue of the object 1 to be examined (for example, to the Larmor frequency of water). The resonant circuit 20 also includes a PIN diode 18 which constitutes the modulation unit 12. The PIN diode 18 is connected, via two resistors or choke coils 17 and a high-ohmic two-wire lead 16, to a control unit 13 which applies a squarewave alternating voltage and hence periodically switches the PIN diode 18 between the off-state and the on-state. It is thus achieved that the coil 11 periodically transmits a signal (in the on-state of the PIN diode 18) and no signal (in the off-state of the PIN diode 18). Because the switching frequency is significantly lower than the resonance frequency of the resonant circuit 20, modulation of the signal induced into the coil 11 takes place; this modulation takes effect essentially as a shift of the signal in the frequency range. The modulation frequency may be chosen to be such that the coil signal is shifted by a known amount in the frequency range, so that the coil signal is separated from the object signal. It is thus achieved that the coil signal can be identified by means of suitable arithmetic means in the receiver unit 7 or the reconstruction unit 8, for example by filtering in the time or frequency domain, and that the position of the coil 11 can be determined from the coil signal and possibly superposed on the MR image.

The receiving coil system 14 is tuned to a sufficiently wide frequency range so as to enable reception of the coil signals in addition to the object signals. During the excitation by the RF transmitter 6, the PIN diode 18 can be adjusted to the off-state so as to prevent local changes of the excitation field strength by the resonant circuit 20. However, the PIN diode 18 may also be in the on-state during the excitation so that a higher signal amplitude is received from the coil 11.

Figure 3:
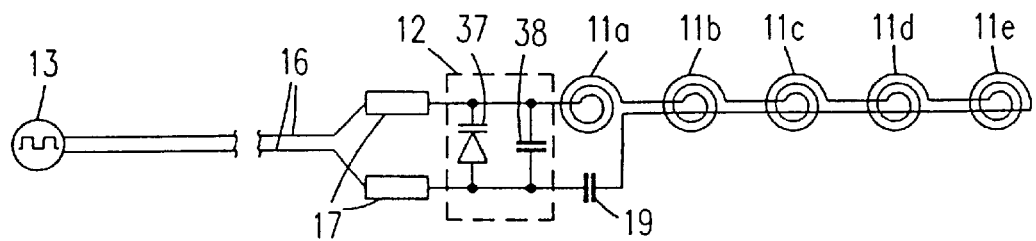
FIG. 3 shows an equivalent diagram of a second embodiment of the invention.

FIG. 3 shows a second embodiment of the invention. Therein, a plurality of microcoils 11a to 11e are connected in series and tuned to the Larmor frequency by means of the capacitor 19. In this case the modulation unit 12 is formed by a varactor (a capacitance diode) 37 and is again connected to the control unit 13 via a high-ohmic control lead 16.

Due to the use of a plurality of microcoils 11a to 11e, arranged along the catheter 10 at small distances of a few millimeters or centimeters, the course of the catheter within the object 1 to be examined can be determined over a longer distance and superposed on the image. In addition to the tuning to the Larmor frequency, in combination with the capacitor 38 and the varactor 37 the capacitor 19 also ensures that the varactor 37 is not DC short-circuited by the coils 11a to 11e. Moreover, during the transmission phase the capacitor 19 provides, in conjunction with the capacitor 38, a subdivision of the induced RF voltage in such a manner that the reduced RF voltage across the varactor 37 is low enough so as to avoid detuning of the varactor or to avoid the generating of undesirable signal components. Moreover, the tuning sensitivity of the resonance frequency may be reduced. In comparison with a PIN diode 18 a varactor 37 offers the essential advantage that its capacitance is voltage-dependent and that, therefore, the resonant circuit can be tuned to the exact Larmor frequency also in the case of manufacturing tolerances of coils and capacitors. In other embodiments, therefore, types of modulation other than by means of a PIN diode are also possible.

In the embodiment shown in FIG. 3, a PIN diode 18 could also be provided instead of the varactor. It would also be possible to provide only one microcoil 11a or a number of microcoils 11a to 11e. The capacitor 38 could also be dispensed with. It is also feasible to connect the capacitor 19 between the upper terminals of the capacitor 38 and the element 37 instead of in the position shown.

Figure 4:
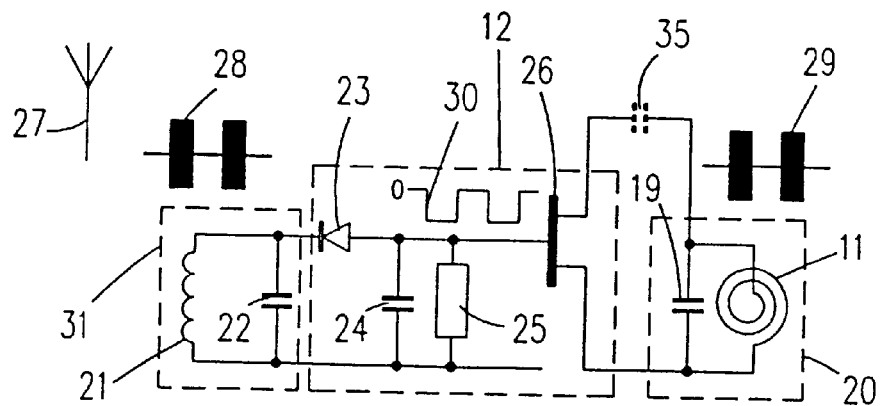
FIG. 4 shows an equivalent diagram of a third embodiment of the invention, involving wireless transport of the control signal.

FIG. 4 shows an embodiment involving wireless control of the modulation unit 12. Therein, a receiver resonant circuit 31 is provided which is formed by a parallel connection of a coil 21 and a capacitor 22, said receiver resonant circuit serving to receive an RF control signal 28 emitted by a transmitter unit 27. The resonant circuit 31 is tuned to the frequency of the RF control signal 28; this frequency lies in a frequency range other than that of the Larmor frequency and that of the resonance frequency of the resonant circuit 20 in order to avoid mutual interference. The RF control signal 28 has a squarewave envelope as shown. In this embodiment the resonant circuit 20 is formed by a parallel connection of the coil 11 and a capacitor 19.

The modulation unit 12 connected to the resonant circuit 31 in this case includes a field effect transistor 26 whose gate G carries a gate voltage 30 which periodically switches the transistor 26 to the low-ohmic state and the high-ohmic state. Using a diode 23, connected to the resonant circuit 31, and a parallel connection of a capacitor 24 and a resistor 25, the gate voltage 30 is derived from the RF control signal 28 which is received by the resonant circuit 31. Because of the periodic switching over of the transistor 26, the desired modulation is imposed on the resonant circuit 20, the modulation frequency being adjustable by way of the frequency of the squarewave envelope of the RF control signal 28.

Instead of a field effect transistor 26, the embodiment shown may also be provided with a different, controllable resistance or switching element which can be periodically switched to a conductive and a non-conductive state or a high-ohmic and a lowohmic state by means of a control voltage. Furthermore, between the drain terminal D of the transistor 26 and the resonant circuit 20 there may be provided a capacitor 35 (denoted by a dashed line) whereby the coil 11 can be tuned to two different resonance frequencies: to a first resonant frequency by means of only the capacitor 19 (in the off-state of the transistor 26) and to a second resonance frequency by means of the parallel connection of the capacitors 19 and 35 (in the on-state of the transistor 26). The coil 11 then emits alternately with different phases and possibly also with different amplitudes, so that the emitted signal can again be identified in the MR signal received.

The resonant circuit 20 in a preferred embodiment can be tuned in such a manner that in the two tuned states the same signal amplitudes are obtained but an opposed phase difference (relative to the phase when the resonant circuit 20 is tuned to the Larmor frequency). Pure phase modulation is thus achieved.

Figure 5:
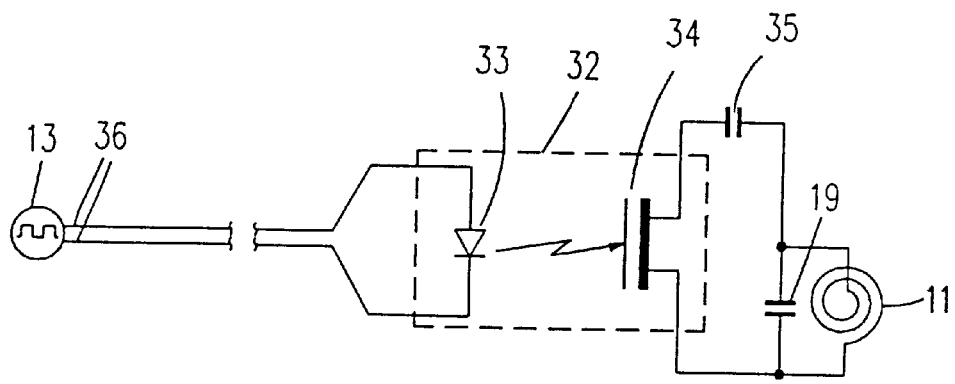
FIG. 5 shows an equivalent diagram of a fourth embodiment of the invention, involving optical transport of the control signal.

FIG. 5 shows an embodiment which includes an optical control lead 36 between the control unit 13 and the modulation unit 32. The control leads 36, which may be, for example thin fiber glass cables, are connected to a light-emitting diode 33. The latter diode generates an optical control signal whereby an appropriate, optically controllable switching element, for example an optically controllable transistor 34, is controlled and hence periodically set to the turned-on and the turned-off state. The remainder of the operation is essentially the same as described with reference to FIG. 4.

The use of a single component for the modulation unit 32, for example a suitable optocoupler, is also feasible.

In addition to the described embodiments, further embodiments of the modulation unit are also feasible. For example, the control unit 13 could be arranged completely within the introduceable part 10a (see FIG. 1) of the medical instrument 10, for example as an integrated squarewave modulator provided with a built-in battery.

Furthermore, a frequency converter circuit with amplifiers could be integrated in the medical instrument 10. Moreover, other circuit arrangements with elements other than the PIN diode, the varactor or the transistor shown are also feasible.

Figure 6:
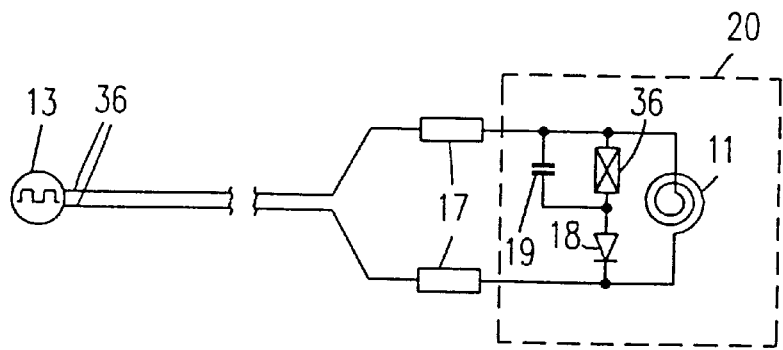
FIG. 6 shows an equivalent diagram of an embodiment of the invention which includes means for reducing the damping of the resonant circuit.

FIG. 6 shows an embodiment which includes means for enhancing the Q of the resonant circuit 20. In this embodiment an element 36, having a negative resistance (a negative impedance converter), is connected parallel to the capacitor 19, said element causing a reduction of the attenuation of the resonant circuit and hence an increase of the Q of the resonant circuit 20. This offers the advantage that the coil 11 can couple a substantially stronger signal into the receiving coil system. The element 36 can be. implemented in various ways, for example. as a retrocoupled field effect transistor.

Referring to the FIGS. 7 and 8, the method according to the invention will be described in detail hereinafter and the different types of modulation that can be converted by means of the embodiments shown in the FIGS. 2 to 6 will also be elucidated.

Figure 7:
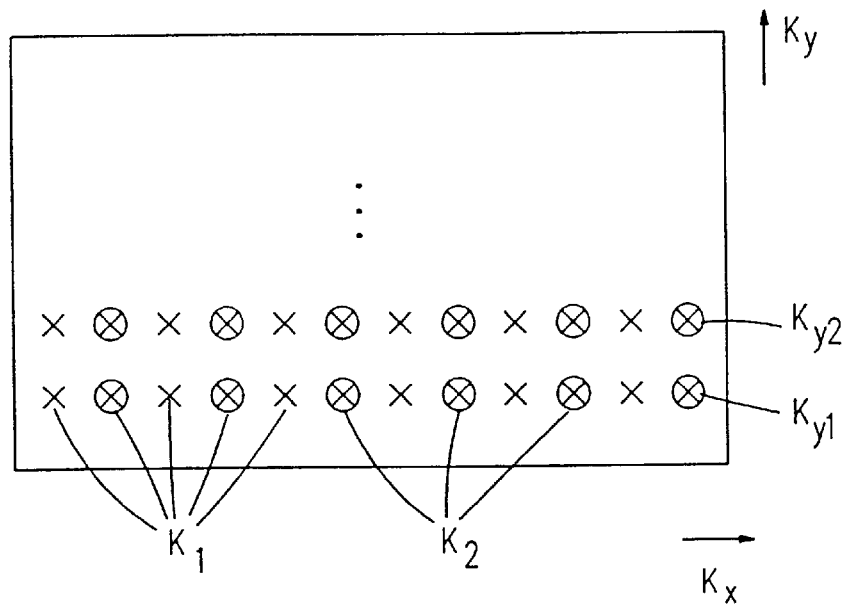
FIG. 7 shows the k-space in order to illustrate the method according to the invention.
Figure 8:
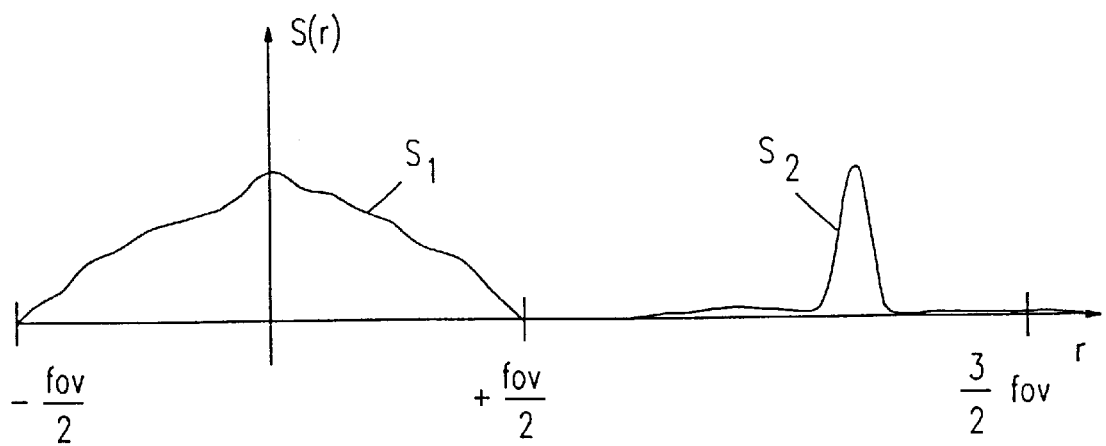
FIG. 8 shows measured signals.

FIG. 7 shows the k-space (spatial frequency space) which must be scanned with a suitable density in order to form an MR image. In the example shown, the k-space is scanned along parallel lines which extend in the $k_x$ direction. The scanning rate is adjusted so that the MR signal, measured by the receiving coil system and comprising the object signal and the coil signal, is sampled at regular intervals in time in the positions (x) denoted by the reference $k_1$. For the present example the modulation frequency was chosen to be such that the coil 11 supplies a signal only every other sampling instant, so only in the positions denoted by $k_2(0)$. This can be achieved, for example by deriving the control signal of the control unit 13 from the sampling rate by frequency halving. Because the coil supplies a signal only every second sampling point $k_2$, it is the same as sub-sampling in relation to the object signal which supplies a signal at every sampling point $k_1$. This causes a repeat of the image of the coil in a different position in space. The described selection of the modulation frequency yields an image $S_2$ of the coil in the space (r) which has been horizontally offset by exactly one half image width. If the sampling rate is selected to be twice as high (oversampling), as required for imaging (of the field of view or FOV), the width of the resultant MR image will be twice that of a conventional MR image (enlargement in the readout direction), the object itself being imaged between −fov/2 and +fov/2 ($S_1$) (see FIG. 8), whereas only the coil is imaged between +½fov and ⅔fov. The coil can then be simply identified and its position determined in this image half and possibly reproduced in the other image half.

The modulation frequency may also be chosen to be such that the coil does not supply a signal every second sampling instant (at the positions $k_2$ in FIG. 7), but only along every second horizontal k-line, be it in that case at all sampling instants $k_1$, for example in such a manner that the coil supplies a signal only along the lines $k_{y1}$, $k_{y3}$, etc., but not along the lines $k_{y2}$, $k_{y4}$, etc. Thus, a further image of the coil is obtained which has been vertically offset by exactly one half image height (enlargement of the image in the phase encoding direction). Via a suitable selection of the FOV or the number of k-lines measured, it can be achieved that the additional image of the coil appears in an otherwise "empty" image area, thus enabling simple identification and localization of the coil.

The modulation could also be performed in such a manner that the resonant circuit is controlled so that the coil is tuned alternately to the Larmor frequency and to a frequency other than the Larmor frequency. It is also feasible to control the modulation unit by means of a sinusoidal or another control voltage in such a manner that a phase and/or frequency modulation is imposed on the resonant circuit.

Phase modulation can be achieved, for example by making the modulation unit control the resonant circuit in such a manner that the coil is tuned alternately to a frequency above and to a frequency below the Larmor frequency, the spacing between the resonance frequencies and the Larmor frequency preferably being chosen to be approximately equal, so that in both cases an approximately equal signal amplitude is obtained. Even though the amplitude of the transmitted signal thus becomes slightly lower than in the case of resonance, a transmitted signal will now occur in both switching states. The two states deviate from the phase position in the case of resonance by each time ±ϕ, for example by ±45°, so that overall a phase difference of 2ϕ occurs, for example a phase difference of 90°. This phase difference can be used to determine the coil signal by differentiation of two measured MR signals with different phases and to calculate the position of the coil therefrom. This method is also suitable for use in the case of a projection and reconstruction method and in the case of radial scanning of the k-space.

The invention is by no means restricted to a given type of scanning of the k-space, to the described types of modulation and to the embodiments shown. It is only essential that the modulation unit modulates the oscillation of the resonant circuit in one way or another in such a manner that the coil signal can be separated from the measured MR signal and that the position of the coil can be determined therefrom.

The kind and the number of coils used for the coil system (systems) is not relevant to the invention either. For example, instead of the microcoils used, coils having a larger diameter or coil systems comprising three coils with mutually perpendicular coil axes could be used, said coils being arranged adjacent one another or around a common center.

It is also feasible to operate a plurality of resonant circuits with a respective coil system (for example, each comprising a respective microcoil) in parallel by means of a respective associated modulation unit and to modulate the resonant circuits differently (for example, by means of different frequencies) so that the coil signals of the coil systems appear in different image areas of the MR image and hence the individual coil systems can be identified and localized.

All references cited herein are incorporated herein by reference in their entirety and for all purposes to the same extent as if each individual publication or patent or patent application was specifically and individually indicated to be incorporated by reference in its entirety for all purposes.

What is clamed is:

1. A magnetic resonance (MR) device which is provided with a medical instrument which is to be introduced into an object to be examined, the medical instrument comprising a receiving coil system which is arranged in the instrument including a coil system comprising at least one coil for receiving and/or transmitting an RF signal as a resonant circuit in conjunction with a capacitor, and wherein the receiving coil system further comprises a modulation unit for modulating an RF signal coupled into the coil system.

2. An MR device as claimed in claim 1, wherein the modulation unit, the capacitor and the coil system are arranged at a small distance from one another and in or on the part of the instrument that can be introduced into the object to be examined.

3. An MR device as claimed in claim 1, wherein a control lead is provided for connection between a control unit for controlling the modulation unit and the modulation unit.

4. An MR device as claimed in claim 3, wherein the control lead is an optical fiber cable and wherein the modulation unit is arranged to convert an optical control signal into an electrical control signal.

5. An MR device as claimed in claim 1, wherein the modulation unit includes a switch arrangement.

6. An MR device as claimed in claim 1, wherein there is provided an RF receiving device for receiving an RF control signal transmitted by an RF control unit, and wherein the modulation unit includes means for converting the RF control signal into a modulation signal for the resonant circuit.

7. An MR device as claimed in claim 6, wherein the RF control unit and the modulation unit are arranged for wireless transmission of the RF control signal.

8. An MR device as claimed in claim 1, wherein the coil system comprises a plurality of coils which are connected in series.

9. An MR device as claimed in claim 1, wherein a plurality of resonant circuits, each of which includes an associated modulation unit, are arranged in or on the instrument, and wherein the RF signals coupled into the coil system are modulated differently.

10. A medical instrument for introduction into an object to be examined by magnetic resonance (MR) imaging comprising a receiving coil system which includes a coil system comprising at least one coil for receiving and/or transmitting an RF signal, wherein the coil system constitutes a resonant circuit in conjunction with a capacitor, and wherein the receiving coil system further includes a modulation unit for modulating an RF signal coupled into the coil system.

11. A method of determining the position of a medical instrument in an object to be examined by magnetic resonance (MR) imaging comprising:

introducing the medical instrument into the object to be examined arranged in the examination zone of an MR device, modulating an RF signal coupled into a receiving coil system of the MR device which includes a coil system comprising at least one coil for receiving and/or transmitting an RF signal and constitutes a resonant circuit in conjunction with a capacitor, the receiving coil system being arranged in the medical instrument, and determining the position of the medical instrument from an MR signal comprising a modulated coil signal received by the receiving coil system.

12. A method as claimed in claim 11, wherein said modulating comprises switching on and off the oscillation of the resonant circuit at a switching frequency.

13. A method as claimed in claim 11, wherein said modulating comprises tuning the resonant circuit alternately to a frequency which is equal to and to a frequency which is not equal to the frequency of the rf signal coupled into the coil system.

14. a method as claimed in claim 11, wherein said modulating comprises tuning the resonant circuit alternately to a frequency above or unequal to the frequency of the rf signal coupled into the coil system.

15. The MR device of claim 5 wherein the switch arrangement comprises a diode, a varactor, a transistor, or an integrated switching element.

16. The MR device of claim 6 wherein the RF receiving device comprises a receiver resonant circuit with a coil and a capacitor.

17. The MR device of claim 8 wherein the coils of the plurality of coils are arranged at a small distance from one another.

18. The medical instrument of claim 10 further comprising a catheter or an endoscope.

* * * * *